US006851429B2

United States Patent
Bishop

(10) Patent No.: US 6,851,429 B2
(45) Date of Patent: Feb. 8, 2005

(54) FACE MASKS

(75) Inventor: Giles Andrew Bishop, Canterbury (GB)

(73) Assignee: Smiths Group Plc, London (GB)

( * ) Notice: Subject to any disclaimer, the term of this patent is extended or adjusted under 35 U.S.C. 154(b) by 79 days.

(21) Appl. No.: 10/142,978

(22) Filed: May 13, 2002

(65) Prior Publication Data

US 2002/0185134 A1 Dec. 12, 2002

(30) Foreign Application Priority Data

Jun. 7, 2001 (GB) .............................................. 0114368

(51) Int. Cl.⁷ .............................................. A62B 18/02
(52) U.S. Cl. ............................ 128/206.25; 128/206.24; 128/206.21; 128/205.25
(58) Field of Search ...................... 128/206.25, 205.25, 128/207.13, 206.21, 206.23, 206.24

(56) References Cited

U.S. PATENT DOCUMENTS

| 2,931,356 | A | | 4/1960 | Schwarz |
| 3,357,426 | A | | 12/1967 | Cohen |
| 4,606,670 | A | * | 8/1986 | Angell ........................ 403/291 |
| 4,907,584 | A | * | 3/1990 | McGinnis .............. 128/206.24 |
| 5,243,971 | A | * | 9/1993 | Sullivan et al. ........ 128/205.25 |
| 5,540,223 | A | | 7/1996 | Starr et al. |
| 5,918,598 | A | * | 7/1999 | Belfer et al. ........... 128/206.25 |
| 6,341,606 | B1 | * | 1/2002 | Bordewick et al. .... 128/206.25 |
| 6,412,487 | B1 | * | 7/2002 | Gunaratnam et al. .. 128/206.24 |
| 6,494,206 | B1 | * | 12/2002 | Bergamaschi et al. . 128/206.24 |
| 6,615,832 | B1 | * | 9/2003 | Chen ..................... 128/206.26 |

FOREIGN PATENT DOCUMENTS

| GB | 2337465 | 11/1999 |
| WO | WO 99/25410 | 5/1999 |

* cited by examiner

Primary Examiner—Glenn K. Dawson
Assistant Examiner—Darwin P Erezo
(74) Attorney, Agent, or Firm—Louis Woo

(57) ABSTRACT

A face mask is provided in two parts. One part is an adhesive ring that is secured around the nose and mouth of the user. The other part is a transparent canopy with a gas port that is a removable clip fit with the ring. When ventilation is not required, the canopy is removed, leaving the ring in position. The canopy can be clipped back onto the ring when ventilation is required.

14 Claims, 3 Drawing Sheets

FACE MASKS

BACKGROUND OF THE INVENTION

This invention relates to face masks for use in supplying breathing gas.

A conventional face mask has a cone-shape canopy with a soft cuff extending around its edge, which is applied against the skin of the patient around the nose and mouth. A port opens into the interior of the canopy so that air or other gas can be supplied to the patient's nose and mouth. Face masks are also used to supply breathing gas to pilots and, for example, to people working in a hazardous atmosphere. Usually, these face masks are held against the face manually or by means of a strap extending around the patient's head. The pressure needed to ensure an effective seal can cause damage to the patient's skin. It can also be difficult to achieve an effective seal without applying manual pressure and this is a disadvantage because it occupies a nurse or clinician. Facial hair can make it even more difficult to achieve a good seal. Alternatively, it has been proposed in U.S. Pat. No. 3,357,426 and WO99/25410 that a face mask be secured to the patient's face by means of an adhesive. Although adhesive attachment has certain advantages, it is not generally suitable where the mask needs to be repeatedly applied to and removed from the face.

BRIEF SUMMARY OF THE INVENTION

It is an object of the present invention to provide an alternative face mask.

According to the present invention there is provided a face mask comprising a ring member adapted to be secured on the face and extend around the openings of the nose and or alternatively the mouth of a user, and a canopy member having a gas port and a peripheral edge adapted to make a removable sealing connection with the ring member such that the canopy member can be removed from the ring member to leave the ring member secured on the face.

The ring member preferably has an adhesive on a surface facing the skin. The adhesive is preferably a moldable material and may be a gel or putty and may be a material that sets on exposure to air. The ring member may include a key and keyway engaged by the adhesive. The ring member and canopy preferably have interengaging surface formations, such as a channel and an edge inserted in the channel. The ring member may be shaped to extend around both the mouth and the openings of the nose, or it may be shaped to extend around just the mouth or just the openings of the nose. The canopy is preferably transparent.

A face mask according to the present invention, will now be described, by way of example, with reference to the accompanying drawings.

DETAILED DESCRIPTION OF THE PREFERRED EMBODIMENTS

With reference to FIGS. 1 to 4, the face mask comprises two separate parts that can be connected or disconnected as desired, namely a ring member 1 and a canopy member 2.

Figure 1:
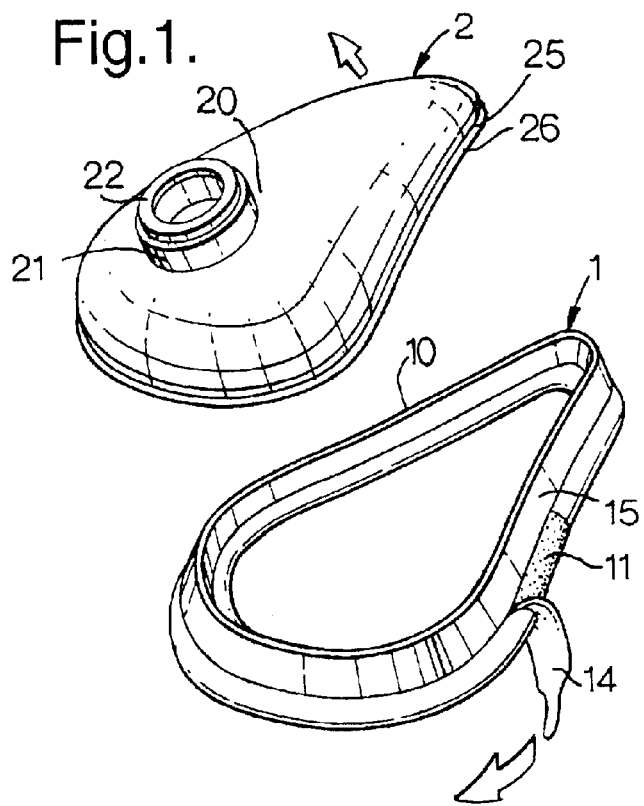
FIG. 1 is a perspective view of mask in two parts before use.
Figure 2:
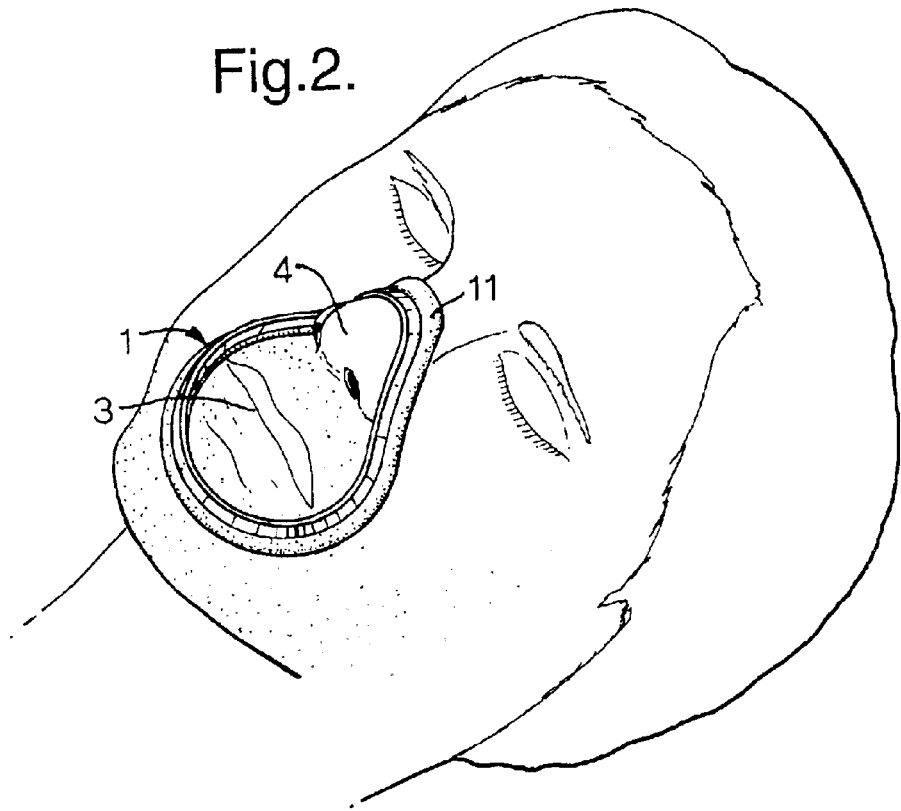
FIG. 2 shows the face mask ring applied to the face.
Figure 3:
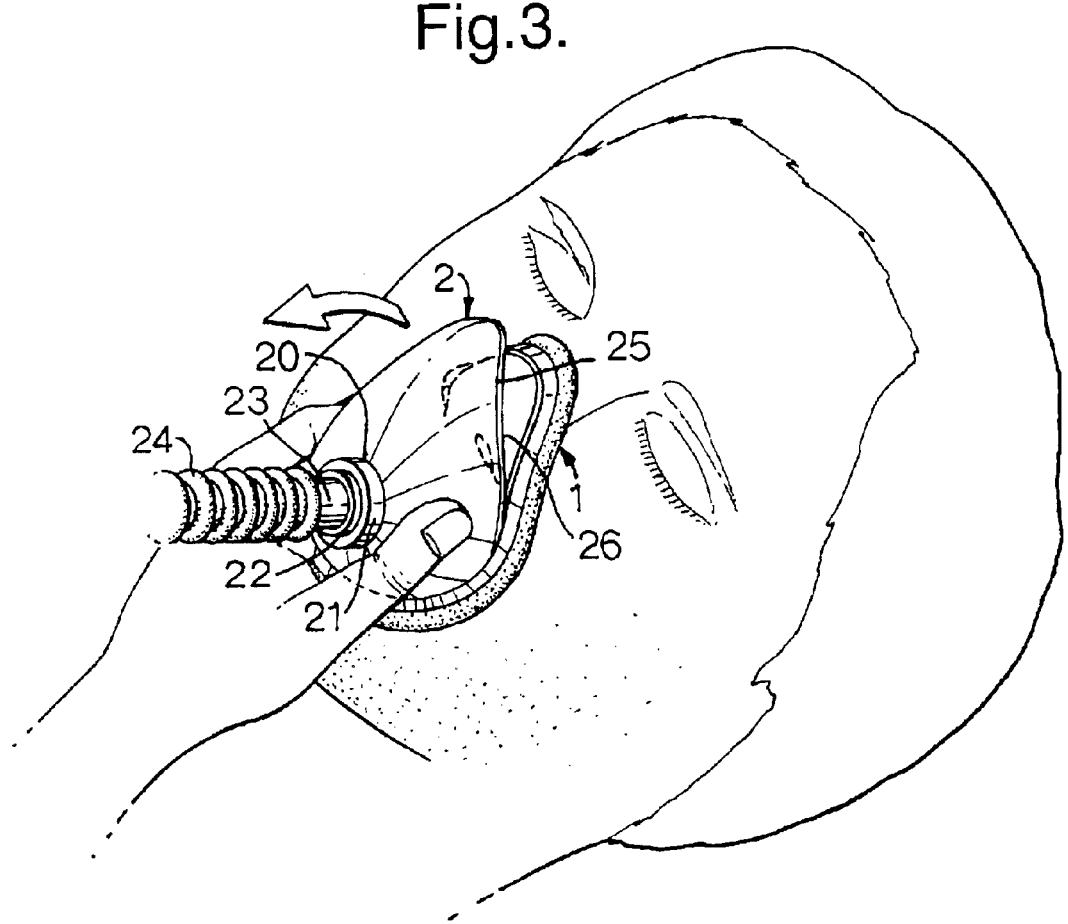
FIG. 3 is a perspective view showing connection/disconnection of the two parts of the mask.
Figure 4:
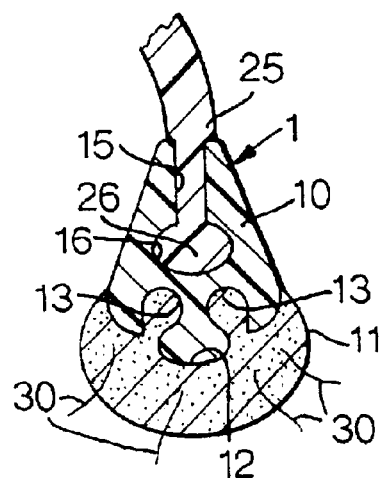
FIG. 4 is a sectional view across the interconnection of the ring and canopy.

The ring member 1 forms a complete loop of pear shape that, in use, encompasses the mouth 3 and nostrils of the nose 4 of the patient. The ring member 1 is relatively shallow and comprises a relatively soft, bendable plastics frame 10 of substantially triangular section supporting an adhesive flange 11 on its lower surface. The flange 11 is made of a soft, putty-like gel material that sets to a rubbery consistency when exposed to air. This material could be of the kind used to form dental impressions. The flange 11 is retained with the frame 10 by means of key and key-way shape formations 12 and 13 (FIG. 4) around the lower edge of the frame so that the flange material fills the key-ways to resist removal. Before use, the flange 11 is protected from air by a removable release strip or cover 14 that can be peeled off before use (FIG. 1). The upper end of the frame 10 has a recess or channel 15 formed around the ring member 1, the channel having a laterally enlarged portion 16 at its lower end.

The canopy member 2 is of a relatively stiff, transparent plastics material and is shaped like a conventional face mask with a generally oval, domed surface the highest point 20 of which is displaced towards the end of the canopy closer the mouth 3. At this point 20, the canopy member 2 has a gas port opening 21 provided by an outwardly-projecting coupling 22 shaped to receive a cooperating coupling 23 at the end of ventilation tubing 24. Around its lower edge 25, the canopy has an enlarged bead 26. The lower edge 25 of the canopy member 2 and the channel 15 of the ring member 1 are shaped to form a mechanical interconnection by engagement of the bead 26 in the enlarged portion 16 of the channel.

The ring 1 can be fitted to the patient's face before connecting the canopy 2. The release strip 14 is removed so that the adhesive flange 11 is exposed and the ring 1 is pressed down onto the patient's face, around the mouth 3 and across the bridge of the nose 4 above the nostril openings. The ring 1 can be bent so that the adhesive flange 11 is urged into close contact with the skin surface to achieve an effective seal. When released, the ring 1 resumes its natural shape with any variations in contour between the skin surface and the lower surface of the ring being accommodated by deformation of the adhesive or the skin. The relatively thick, putty-like nature of the uncured adhesive 11 enables facial hair 30 to extend within the thickness of the adhesive and allows the adhesive to contact the skin surface. After a short period of time the adhesive 11 cures to a rubbery consistency forming an effective mechanical bond and gas-tight seal with the skin.

The clinician then takes the canopy 2 with the ventilation tubing 24 attached and holds it up to the ring 1, aligning the bead 26 on the canopy with the channel 15 in the ring. The canopy 2 is pushed firmly against the ring 1 so that the bead 26 snaps as a push fit into the enlarged portion 16 of the channel 15. The engagement of the bead 26 in the channel 15 forms a secure mechanical connection between the canopy 2 and the ring 1 and forms an effective gas seal. This connection is sufficient to hold the face mask securely on the face in normal use.

The canopy 2 can be removed from the ring 1 whenever required, either by the clinician or the patient himself, simply by peeling the canopy away from the ring at one end. The canopy 2 can subsequently be replaced on the ring if ventilation is needed again.

The face mask enables reliable ventilation via the mouth and nose without the need for continuous manual pressure and without the need for straps or the like, which can cause skin damage after prolonged use. The mask can be readily removed and replaced without compromising the effectiveness of the seal. The mask is particularly useful for patients with facial hair.

Figure 5:
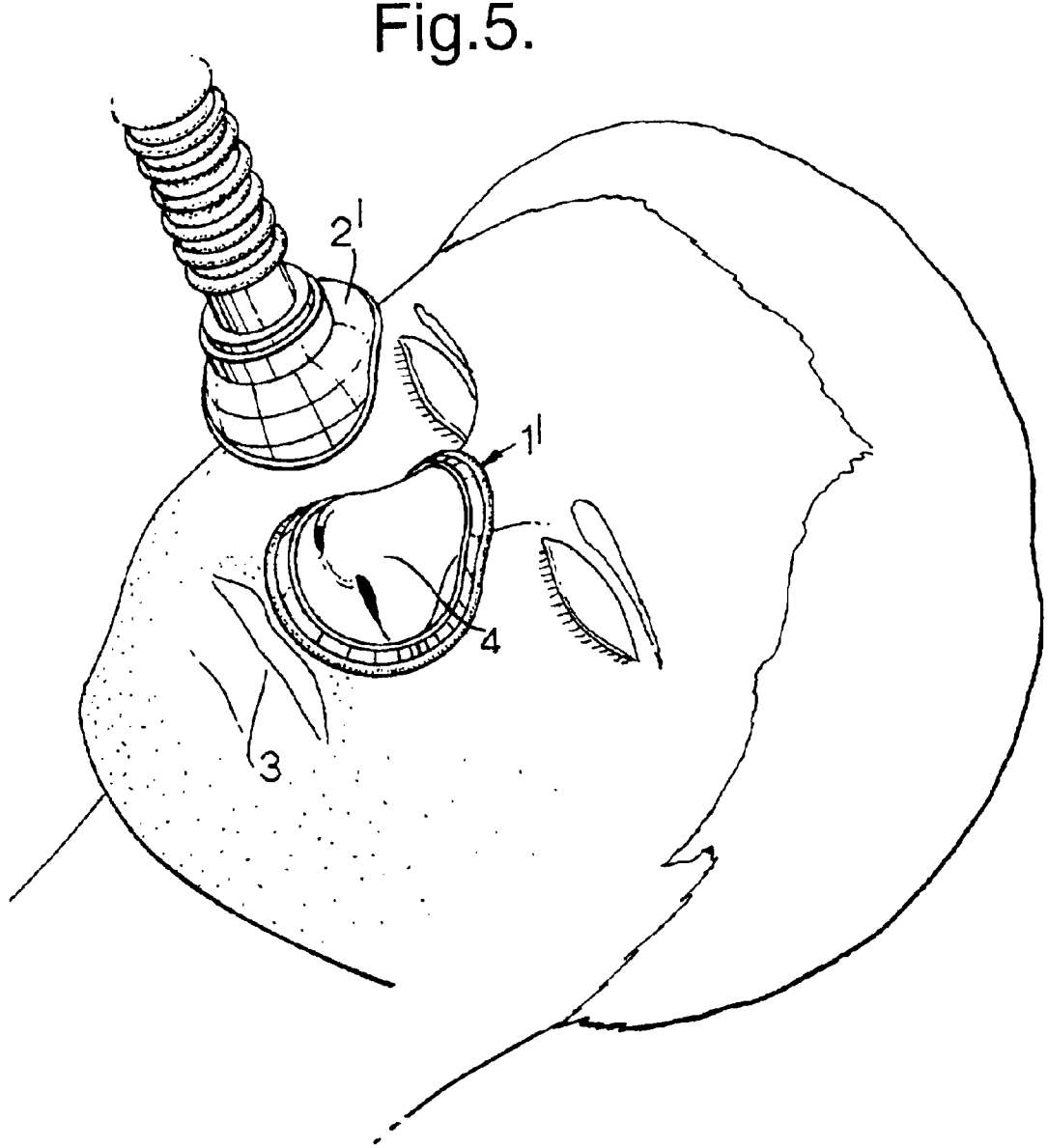
FIG. 5 shows a modification of the mask.

The face mask need not necessarily fit around the openings of both the nose and mouth. It could, for example, fit around only the mouth or, as shown in FIG. 5, around only the nose 4. In this arrangement, the ring 1' is smaller and is secured to the skin of the face around the nose 4, above the mouth 3. The canopy 2' is shaped to cover only the nose 4, leaving sufficient clearance for gas flow. The canopy 2' clips onto the ring 1' in the same way as the larger combined nose and mouth face mask shown in FIGS. 1 to 4.

What I claim is:

1. A face mask comprising: a ring member, said ring member being adapted to be secured on a user's face and extend around openings of the user's nose and or alternatively the mouth, and said ring member having first and second opposed surfaces, said first surface supporting an adhesive material arranged to secure with the user's skin, said second surface having an interengaging surface formation; a canopy member, said canopy member having a gas port and a peripheral edge with an interengaging surface formation adapted to make a removable, interengaging sealing connection with said interengaging surface formation on said ring member such that the canopy member can be removed from said ring member to leave said ring member secured on the face.

2. A face mask according to claim 1, wherein said ring member has an adhesive on a surface facing the user's skin.

3. A face mask according to claim 2, wherein said adhesive is a mouldable material.

4. A face mask according to claim 2, wherein said adhesive is a gel or putty.

5. A face mask according to claim 2, wherein said adhesive is a material that sets on exposure to air.

6. A face mask according to claim 2, wherein said ring member includes a key and keyway engaged by said adhesive.

7. A face mask according to claim 1, wherein said canopy is transparent.

8. A face mask according to claim 1, wherein said interengaging surface formations include a channel and an edge inserted in said channel.

9. A face mask according to claim 1, wherein said ring is shaped to extend around both the mouth and the openings of the nose.

10. A face mask according to claim 1, wherein said ring is shaped to extend around just the mouth.

11. A face mask according to claim 1, wherein said ring is shaped to extend around just the openings of the nose.

12. A face mask comprising: a bendable ring member, said ring member having first and second opposed surfaces, said first surface supporting an adhesive surface adapted to be secured on a user's face and extend around openings of the user's mouth, said second surface having an interengaging surface formation; a canopy member, said canopy member having a gas port and a peripheral edge with an interengaging surface formation adapted to make a removable, interengaging, push-fit sealing connection with said interengaging surface formation on said ring member such that the canopy member can be removed from said ring member to leave said ring member adhesively secured on the face.

13. A face mask comprising: a bendable ring member, said ring member having first and second oposed surfaces, said first surface supporting an adhesive surface adapted to be secured on a user's face and extend around openings of the user's nose and mouth, said second surface having an interengaging surface formation; a canopy member, said canopy member having a gas port and a peripheral edge with an interengaging surface formation adapted to make a removable, interengaging, push-fit sealing connection with said interengaging surface formation on said ring member such that the canopy member can be removed from said ring member to leave said ring member adhesively secured on the face.

14. A face mask comprising: a bendable ring member, said ring member having first and second opposed surfaces, said first surface supporting an adhesive surface adapted to be secured on a user's face and extend around openings of the user's nose, said second surface having an interengaging surface formation; a canopy member, said canopy member having a gas port and a peripheral edge with an interengaging surface formation adapted to make a removable, interengaging, push-fit sealing connection with said interengaging surface formation on said ring member such that the canopy member can be removed from said ring member to leave said ring member adhesively secured on the face.

* * * * *